United States Patent
Kong et al.

(10) Patent No.: US 10,743,841 B2
(45) Date of Patent: Aug. 18, 2020

(54) METHOD OF DISPLAYING ELASTOGRAPHY IMAGE AND ULTRASOUND DIAGNOSIS APPARATUS PERFORMING THE METHOD

(71) Applicant: SAMSUNG ELECTRONICS CO., LTD., Suwon-si (KR)

(72) Inventors: Dong-geon Kong, Hwaseong-si (KR); Jun-ho Park, Hwaseong-si (KR); Hyoung-ki Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1178 days.

(21) Appl. No.: 14/996,618

(22) Filed: Jan. 15, 2016

(65) Prior Publication Data
US 2016/0331345 A1    Nov. 17, 2016

(30) Foreign Application Priority Data
May 14, 2015  (KR) .................. 10-2015-0067595

(51) Int. Cl.
*A61B 8/00* (2006.01)
*A61B 8/08* (2006.01)

(52) U.S. Cl.
CPC .............. *A61B 8/485* (2013.01); *A61B 8/463* (2013.01); *A61B 8/5207* (2013.01); *A61B 8/5215* (2013.01)

(58) Field of Classification Search
CPC ................................ A61B 8/485; A61B 8/463
See application file for complete search history.

(56) References Cited

U.S. PATENT DOCUMENTS

| 6,558,324 B1 | 5/2003 | Von Behren et al. |
| 8,098,921 B2 | 1/2012 | Matsumura |

(Continued)

FOREIGN PATENT DOCUMENTS

| CN | 101175444 A | 5/2008 |
| CN | 101370431 A | 2/2009 |

(Continued)

OTHER PUBLICATIONS

Notice of Allowance dated Jul. 18, 2016, issued by the Korean Intellectual Property Office in corresponding Korean Application No. 10-2015-0067595.

(Continued)

*Primary Examiner* — Joseph M Santos Rodriguez
(74) *Attorney, Agent, or Firm* — Sughrue Mion, PLLC

(57) ABSTRACT

A method of displaying an elastography image and an ultrasound diagnosis apparatus performing the method are provided. The method includes transmitting an ultrasound signal to an object, receiving a response signal to the transmitted ultrasound signal, determining ultrasound image data based on the received response signal, determining displacement image data based on the determined ultrasound image data, generating elastography images based on the determined displacement image data, dividing the elastography images into sections based on a criterion, and determining a representative elastography image of each of the sections based on one or more elastography images in each of the sections and quality information of the one or more elastography images, the quality information being based on a strain of a first elastography image among the one or more elastography images. The method further includes displaying the representative elastography image.

28 Claims, 17 Drawing Sheets

(56) References Cited

U.S. PATENT DOCUMENTS

| | | |
|---|---|---|
| 8,852,106 B2 | 10/2014 | Kasahara et al. |
| 2009/0105589 A1 | 4/2009 | Osaka et al. |
| 2012/0016237 A1 | 1/2012 | Tanigawa |
| 2012/0253195 A1 | 10/2012 | Inoue et al. |
| 2012/0321165 A1* | 12/2012 | Suda ............ G01S 7/5205 382/131 |
| 2014/0155746 A1 | 6/2014 | Tanigawa |
| 2019/0159762 A1 | 5/2019 | Li |

FOREIGN PATENT DOCUMENTS

| | | |
|---|---|---|
| CN | 102283679 A | 12/2011 |
| CN | 102958450 A | 3/2013 |
| CN | 103845081 A | 6/2014 |
| CN | 103845084 A | 6/2014 |
| EP | 2612600 A1 | 7/2013 |
| JP | 2011-156191 A | 8/2011 |
| KR | 10-2012-0006943 A | 1/2012 |
| KR | 10-2014-0070436 A | 6/2014 |
| WO | 2011/010626 A1 | 1/2011 |
| WO | 2011010626 A1 | 1/2011 |
| WO | 2013/017105 A | 2/2013 |

OTHER PUBLICATIONS

Communication dated Oct. 19, 2016, issued by the European Patent Office in counterpart European Application No. 16169155.5.

Communication dated Mar. 30, 2016 issued by the Korean Intellectual Property Office in counterpart Korean Patent Application No. 10-2015-0067595.

Communication dated May 2, 2016 issued by the International Searching Authority in counterpart International Patent Application No. PCT/KR2016/000282 (PCT/ISA/220, PCT/ISA/210, PCT/ISA/237).

Communication dated Nov. 29, 2019, from the State Intellectual Property Office of People's Republic of China in counterpart Application No. 201680028009.0.

Communication dated Jun. 9, 2020 issued by the State Intellectual Property Office of P.R. China in counterpart Chinese Application No. 201680028009.0.

\* cited by examiner

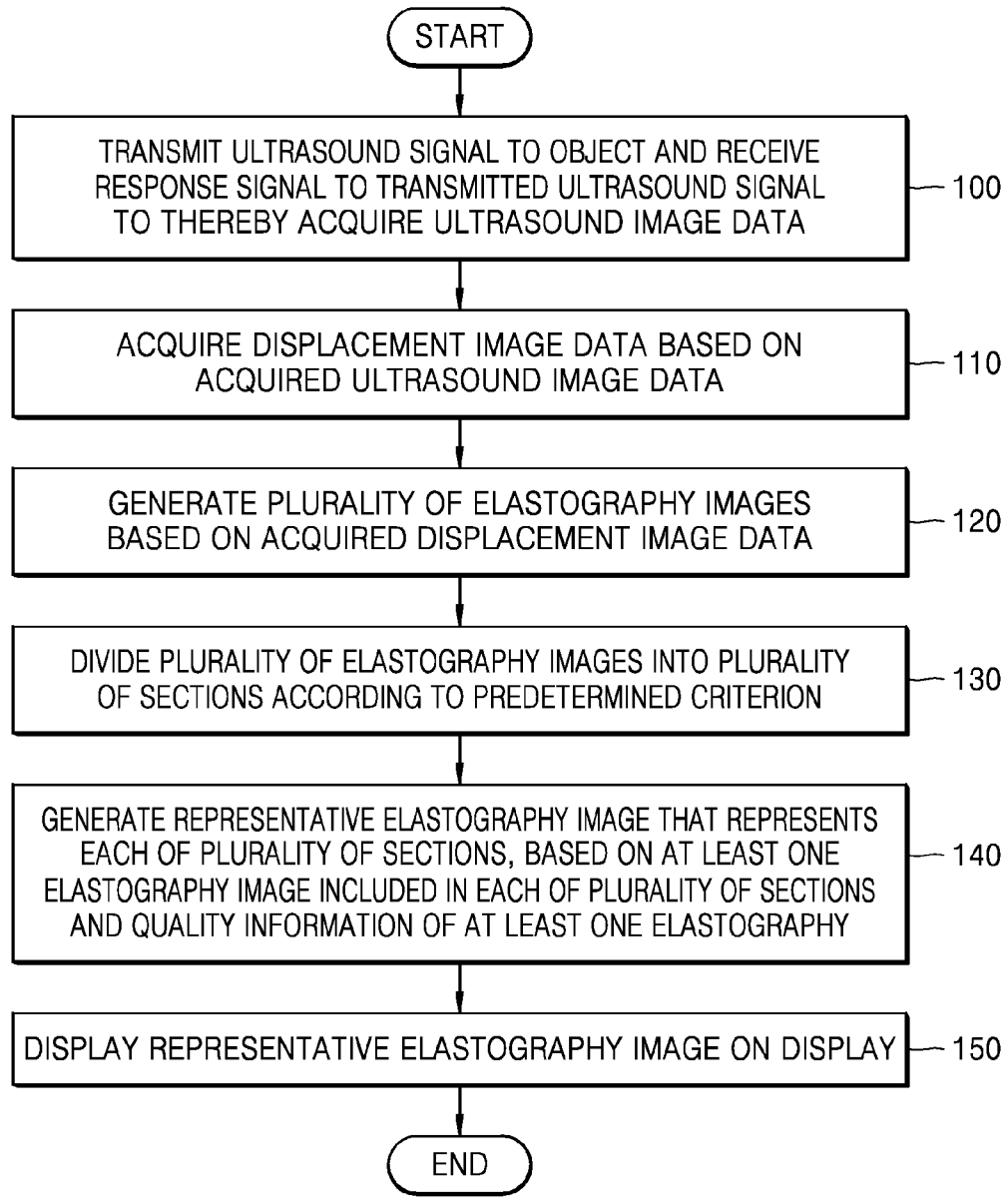

METHOD OF DISPLAYING ELASTOGRAPHY IMAGE AND ULTRASOUND DIAGNOSIS APPARATUS PERFORMING THE METHOD

CROSS-REFERENCE TO RELATED PATENT APPLICATION

This application claims priority from Korean Patent Application No. 10-2015-0067595, filed on May 14, 2015, in the Korean Intellectual Property Office, the disclosure of which is incorporated herein in its entirety by reference.

BACKGROUND

1. Field

Methods and apparatuses consistent with exemplary embodiments relate to methods of and ultrasound diagnosis apparatuses for displaying an elastography image. More particularly, methods and apparatuses consistent with exemplary embodiments relate to a method of acquiring a good-quality elastography image from a plurality of elastography images and displaying the good-quality elastography image, and an ultrasound diagnosis apparatus performing the method.

2. Description of the Related Art

Ultrasound diagnosis apparatuses transmit an ultrasonic signal from the surface of the body of an object toward an inner part of the body by using a probe and obtain an image of a cross-section of a soft tissue or an image of blood flow by using information about an ultrasonic signal reflected by the inner part of the body.

Such ultrasound diagnosis apparatuses are compact and inexpensive and display a captured image in real time. In addition, the ultrasound diagnosis apparatuses are safe due to the lack of radioactive exposure, such as, exposure to X-rays, and thus are widely used together with other image diagnosis apparatuses such as an X-ray diagnosis apparatus, a computed tomography (CT) scanner, a magnetic resonance imaging (MRI) apparatus, a nuclear medical diagnosis apparatus, and the like.

Elastography is an ultrasound imaging modality to represent the elastic properties of an object via an image. The elastic properties of an object provide qualitative or quantitative information about diseases associated with the elasticity of a body tissue, such as cancers and liver cirrhosis.

Tumors are harder than normal tissue. In other words, the elasticity of a tumor is smaller than that of a normal tissue, and thus, when the same pressure is applied to the tumor and the normal tissue, a strain of the normal tissue is greater than that of the tumor. Thus, elastography may be used to diagnose tumors or cancers. Because ultrasound diagnosis apparatuses can be used very conveniently and quickly compared with other medical image diagnosis apparatuses, elastography image technology using ultrasonic waves may be used in the early diagnosis of various diseases.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide methods and apparatuses for displaying an ultrasound elastography image, whereby elastography images are divided into a plurality of sections and a representative elastography image of a good quality is generated and displayed, thereby increasing the accuracy of disease diagnosis and shortening the time for reviewing images.

According to an aspect of an exemplary embodiment, a method of displaying an elastography image includes transmitting an ultrasound signal to an object, receiving a response signal to the transmitted ultrasound signal, determining ultrasound image data based on the received response signal, determining displacement image data based on the determined ultrasound image data, generating elastography images based on the determined displacement image data, dividing the elastography images into sections based on a criterion, and determining a representative elastography image of each of the sections based on one or more elastography images in each of the sections and quality information of the one or more elastography images, the quality information being based on a strain of a first elastography image among the one or more elastography images. The method further includes displaying the representative elastography image.

The quality information may include a difference between the strain of the first elastography image and a strain of a second elastography image different from the first elastography image, the second elastography image including at least one among a previous frame of the first elastography image and a reference elastography image.

The quality information may include at least one among a size of a mean strain of the first elastography image and a correlation coefficient of the first elastography image.

The dividing may include estimating a motion of the object based on the displacement image data, and dividing the elastography images into the sections based on the estimated motion.

The dividing may include dividing the elastography images into the sections based on a number of frames in each of the sections.

The determining the representative elastography image may include selecting, as the representative elastography image, an elastography image having quality information satisfying a condition from the one or more elastography images in each of the sections.

The determining the representative elastography image may include synthesizing the one or more elastography images in each of the sections to generate the representative elastography image.

The displaying may include displaying the representative elastography image together with a real-time ultrasound image that is acquired based on the determined ultrasound image data.

The real-time ultrasound image may include at least one among a real-time elastography image and a real-time brightness mode image.

The displaying may include displaying a representative elastography image of a most recently concluded section among the representative elastography image of each of the sections.

The displaying may include displaying the representative elastography image of each of the sections in a chronological order.

The displaying may include displaying the representative elastography image together with quality information corresponding to each of the elastography images.

The displaying may include displaying the representative elastography image together with displacement image data corresponding to each of the elastography images.

The displacement image data may include a displacement between ultrasound image data that is determined before a tissue of the object is compressed by a probe and ultrasound image data that is determined after the tissue of the object is compressed by the probe.

A non-transitory computer-readable storage medium may store a program including instructions to cause a computer to perform the method.

According to an aspect of an exemplary embodiment, an ultrasound diagnosis apparatus includes an ultrasound transceiver configured to transmit an ultrasound signal to an object, receive a response signal to the transmitted ultrasound signal, and determine ultrasound image data based on the received response signal. The ultrasound diagnosis apparatus further includes an image processor configured to determine displacement image data based on the determined ultrasound image data, generate elastography images based on the determined displacement image data, divide the elastography images into sections based on a criterion, and determine a representative elastography image of each of the sections based on one or more elastography images in each of the sections and quality information of the one or more elastography images, the quality information being based on a strain of a first elastography image among the one or more elastography images. The ultrasound diagnosis apparatus further includes a display configured to display the representative elastography image.

The image processor may be further configured to estimate a motion of the object based on the displacement image data, and divide the elastography images into the sections based on the estimated motion.

The image processor may be further configured to divide the elastography images into the sections based on a number of frames in each of the sections.

The image processor may be further configured to select, as the representative elastography image, an elastography image having quality information satisfying a condition from the one or more elastography images in each of the sections.

The image processor may be further configured to synthesize the one or more elastography images in each of the sections to generate the representative elastography image.

The display may be further configured to display the representative image together with a real-time ultrasound image that is acquired based on the determined ultrasound image data.

The display may be further configured to display a representative elastography image of a most recently concluded section among the representative elastography image of each of the sections.

The display may be further configured to display the representative elastography image of each of the sections in a chronological order.

The display may be further configured to display the representative elastography image together with the quality information corresponding to each of the elastography images.

The display may be further configured to display the representative elastography image together with displacement image data corresponding to each of the elastography images.

According to an aspect of an exemplary embodiment, an ultrasound diagnosis apparatus includes an image processor configured to generate displacement images based on displacements between ultrasound images, generate elastography images based on differences of strains between the displacement images, divide the elastography images into sections, and determine a representative elastography image of each of the sections, the representative elastography image having a lowest difference of strains among one or more elastography images in each of the sections. The ultrasound diagnosis apparatus further includes a display configured to display the representative elastography image.

BRIEF DESCRIPTION OF THE DRAWINGS

The above and/or other aspects will be more apparent by describing exemplary embodiments, with reference to the accompanying drawings, in which:

FIG. 4 is a flowchart of a method of displaying a representative elastography image, according to an exemplary embodiment;

DETAILED DESCRIPTION

Figure 1:
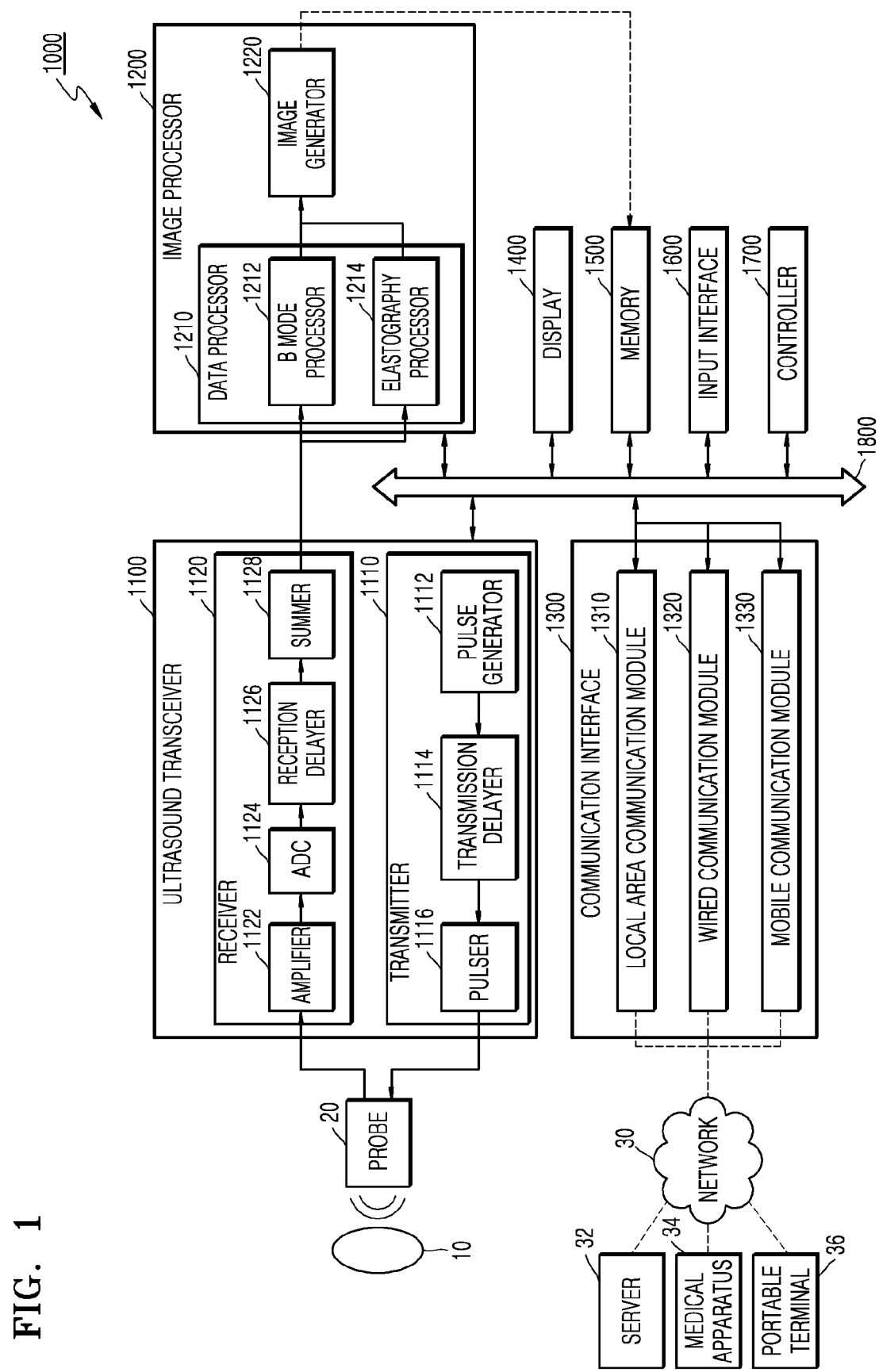
FIG. 1 is a block diagram showing a configuration of an ultrasound diagnosis apparatus, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail since they would obscure the description with unnecessary detail.

It will be understood that the terms "comprises" and/or "comprising" used herein specify the presence of stated features or components, but do not preclude the presence or addition of one or more other features or components. In addition, the terms such as "unit", "-er (-or)", and "module" described in the specification refer to an element for performing at least one function or operation, and may be implemented in hardware, software, or the combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

FIG. 1 is a block diagram showing a configuration of an ultrasound diagnosis apparatus 1000, according to an exemplary embodiment.

Referring to FIG. 1, the ultrasound diagnosis apparatus 1000 includes a probe 20, an ultrasound transceiver 1100, an image processor 1200, a communication interface 1300, a display 1400, a memory 1500, an input interface 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10.

The probe 20 includes a plurality of transducers, and the plurality of transducers oscillates in response to electric signals and generates acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delayer 1114, and a pulser 1116. The pulse generator 1112 generates pulses for forming transmission ultrasound waves based on a predetermined pulse repetition frequency (PRF), and the transmission delayer 1114 delays the pulses by delay times for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 includes an amplifier 1122, an analog-to-digital converter (ADC) 1124, a reception delayer 1126, and a summer 1128. The amplifier 1122 amplifies echo signals in each channel, and the ADC 1124 performs analog-to-digital conversion with respect to the amplified echo signals. The reception delayer 1126 delays digital echo signals output by the ADC 1124 by delay times for determining reception directionality, and the summer 1128 generates ultrasound data by summing the echo signals processed by the reception delayer 1166. In one or more exemplary embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components. Similarly, a Doppler processor may extract Doppler components from ultrasound data, and the image generator 1220 may generate a Doppler image indicating a movement of an object as colors or waveforms based on the extracted Doppler components.

According to an exemplary embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to exemplary embodiments.

The communication interface 1300 is connected to a network 30 by wire or wirelessly to communicate with an external device or a server. The communication interface 1300 may exchange data with a hospital server or another medical apparatus in a hospital, which is connected thereto via a PACS. Furthermore, the communication interface 1300 may perform data communication according to the digital imaging and communications in medicine (DICOM) standard.

The communication interface 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication interface 1300 may receive information about a diagnosis history or medical treatment schedule of a patient from a server and utilizes the received information to diagnose the patient. Furthermore, the communication interface 1300 may perform data communication not only with a server or a medical apparatus in a hospital, but also with a portable terminal of a medical doctor or patient.

The communication interface 1300 is connected to the network 30 by wire or wirelessly to exchange data with a server 32, a medical apparatus 34, or a portable terminal 36. The communication interface 1300 may include one or more components for communication with external devices. For example, the communication interface 1300 includes a local area communication interface 1310, a wired communication interface 1320, and a mobile communication interface 1330.

The local area communication interface 1310 refers to a module for local area communication within a predetermined distance. Examples of local area communication techniques according to an exemplary embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication interface 1320 refers to a module for communication using electric signals or optical signals. Examples of wired communication techniques according to an exemplary embodiment may include communication via a twisted pair cable, a coaxial cable, an optical fiber cable, and an Ethernet cable.

The mobile communication interface 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input interface 1600 refers to a device via which a user inputs data for controlling the ultrasound diagnosis apparatus 1000. The input interface 1600 may include hardware components, such as a keypad, a mouse, a touch pad, a touch screen, and a jog switch. However, exemplary embodiments are not limited thereto, and the input interface 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication interface 1300, the display 1400, the memory 1500, and the input interface 1600 shown in FIG. 1.

All or some of the probe 20, the ultrasound transceiver 1100, the image processor 1200, the communication interface 1300, the display 1400, the memory 1500, the input interface 1600, and the controller 1700 may be implemented as software modules. Also, at least one of the ultrasound transmission/reception unit 1100, the image processor 1200, and the communication interface 1300 may be included in the control unit 1600; however, exemplary embodiments are not limited thereto.

Figure 2A:
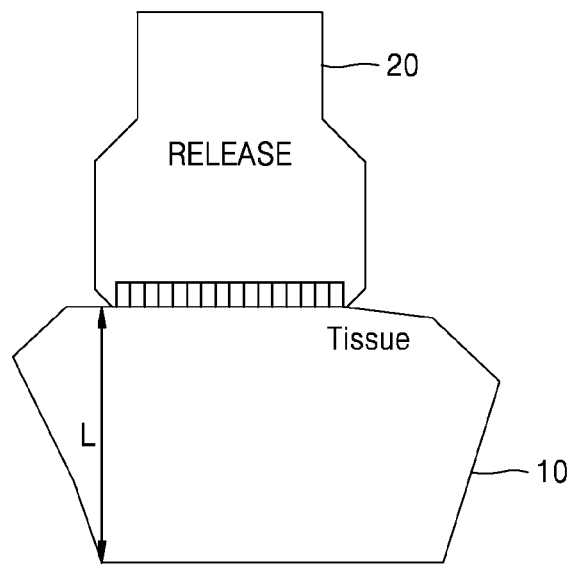
FIGS. 2A and 2B are diagrams showing a tissue of an object being deformed by slowly applying a force to the object, according to an exemplary embodiment.
Figure 2B:
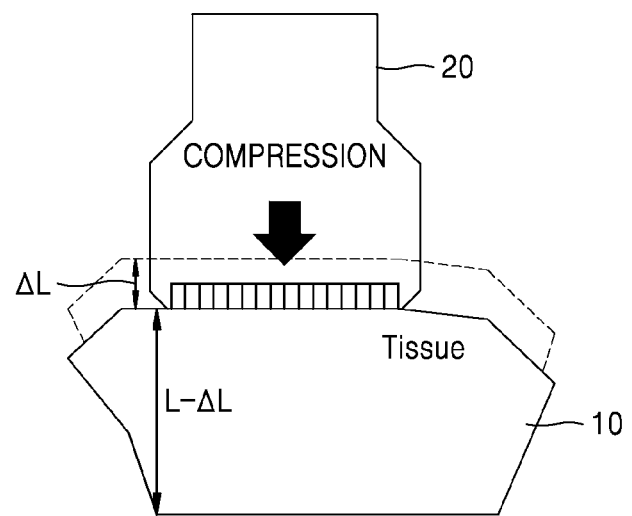

FIGS. 2A and 2B are diagrams showing a tissue of the object 10 being deformed by slowly applying a force to the object 10, according to an exemplary embodiment.

Cancers or tumors generated in a soft tissue of an object, such as the breast or prostate, are harder than a surrounding normal tissue. However, because a boundary between a cancer and surrounding normal tissue is unclear on an ultrasound brightness (B) mode image, it is hard to distinguish the cancer from the surrounding normal tissue. Thus, an ultrasound elastography image capable of being provided with quantitative information obtained by imaging the hardness of tissue may help diagnosis of tumors or cancers.

The ultrasound elastography image is obtained by measuring deformation of tissue of an object due to application of a mechanical force (pressure) and imaging the measured deformation.

In other words, elastography is used to represent the elastic properties of an object via an image. The brightness and/or color of pixels in an elastography image may be controlled according to the elastic properties of an object. The elastic properties of the object may be determined via a strain of the object caused by a pressure applied thereto.

Because a user has difficulty in quantitatively measuring a mechanical force applied to tissue of the object, the user may measure and image only the strain.

As shown in FIG. 2A, tissue of the object 10 has a depth of L before a user applies a mechanical force to the object 10 by using the probe 20. As shown in FIG. 2B, after the user applies a mechanical force to the object 10 by using the probe 20, the tissue of the object 10 is compressed and deformed.

In other words, the tissue is compressed in the direction in which the user applies the mechanical force to the tissue, and thus the tissue of the object 10 has a depth of L-ΔL.

As described above, as compared with the depth of the tissue of the object 10 before the user applies a mechanical force to the object 10 by using the probe 20, the depth of the tissue of the object 10 after the mechanical force is applied to the object 10 has a displacement of ΔL in the direction in which the mechanical force is applied. In other words, referring to FIGS. 2A and 2B, while the user is applying the mechanical force to the object 10 by using the probe 20, displacement occurs due to deformation of the tissue of the object 10.

While the user is applying the mechanical force to the object 10 by using the probe 20, the probe 20 according to an exemplary embodiment transmits an ultrasound signal to the object 10 and receives a response signal reflected by the object 10.

For example, the probe 20 according to an exemplary embodiment may periodically apply a force to a diagnosis part of the object 10 and periodically measure deformation of tissue of the diagnosis part of the object 10.

For example, while a user is periodically applying a force to the diagnosis part of the object 10 by using the probe 20, the probe 20 transmits an ultrasound signal to the object 10 and receives a response signal reflected by the object 10 that periodically repeats compression and release.

An ultrasound diagnosis apparatus according to an exemplary embodiment may acquire ultrasound image data based on the received response signal, and generate a plurality of ultrasound image frames F(i) (1≤i≤N) corresponding to the ultrasound image data. In this case, the ultrasound diagnosis apparatus according to an exemplary embodiment may calculate a displacement between temporally-adjacent ultrasound image frames and acquire displacement image data based on the calculated displacement.

The ultrasound diagnosis apparatus according to an exemplary embodiment may also generate a plurality of displacement image frames $F_d(i)$ (1≤i≤N−1) corresponding to the displacement image data. For example, a displacement image frame $F_d(1)$ is a displacement image frame corresponding to displacement image data calculated between an ultrasound image frame F(1) and an ultrasound image frame F(2), and a displacement image frame $F_d(N-1)$ is a displacement image frame corresponding to displacement image data calculated between an ultrasound image frame F(N−1) and an ultrasound image frame F(N).

When the displacement is differentiated in the direction in which the mechanical force is applied, a strain of the object 10 is calculated. Thus, when a displacement image frame is differentiated in the direction in which the mechanical force is applied, a strain image frame $F_s(i)$ (1≤i≤N−1) may be acquired. An elastography image frame according to an exemplary embodiment may include a strain image frame.

In this case, pixels of the strain image frame may have different degrees of brightness and/or different colors according to strains of the pixels. For example, a location having a small strain on a strain image may be shown darkly.

The object 10 may include tissue of interest that is to be pathologically diagnosed via elastography. For example, the tissue of interest may be a thyroid, a breast, or a prostate, and may include soft tissue such as normal tissue and hard tissues such as cancers or tumors.

In this case, when tissues having different degrees of hardness are distributed in the direction in which a user has applied a force, within the tissue of interest, and a user slowly presses the tissue of the object 10 by using the probe 20, soft tissue is more compressed than hard tissue and is thus greatly deformed. Thus, displacement by which tissue is moved in the direction in which a force is applied varies according to hardness of the tissue, and accordingly a strain of the tissue varies.

For example, when a tumor or a cancer is present between normal tissues of the object 10 and a user slowly presses the tissue of the object 10 by using the probe 20, displacement occurs more greatly in the normal tissues than in the tumor or the cancer. Accordingly, the strain of a tumor is smaller than that of normal tissue, and thus the tumor may be displayed more darkly than the normal tissue on an identical elastography image.

Thus, an ultrasound elastography image may be more helpful in diagnosing a tumor or a cancer, than an ultrasound B mode image from which it is hard to distinguish a cancer from surround normal tissue due to unclearness of the boundary therebetween.

However, images having good-quality elasticity and images having bad-quality elasticity are mixed in a plurality of ultrasound elastography images corresponding to a plurality of frames acquired in real time, and many similar elastography images are repeated. Thus, a user has difficulty in selecting images having good-quality elasticity.

Therefore, the ultrasound diagnosis apparatus 1000 according to an exemplary embodiment automatically selects only an image frame having good-quality elasticity from a plurality of ultrasound elastography image frames and displays the selected image frame having good-quality elasticity on the display 1400 in real time, whereby a user may conveniently make diagnosis by using elastography image frames.

Figure 3:
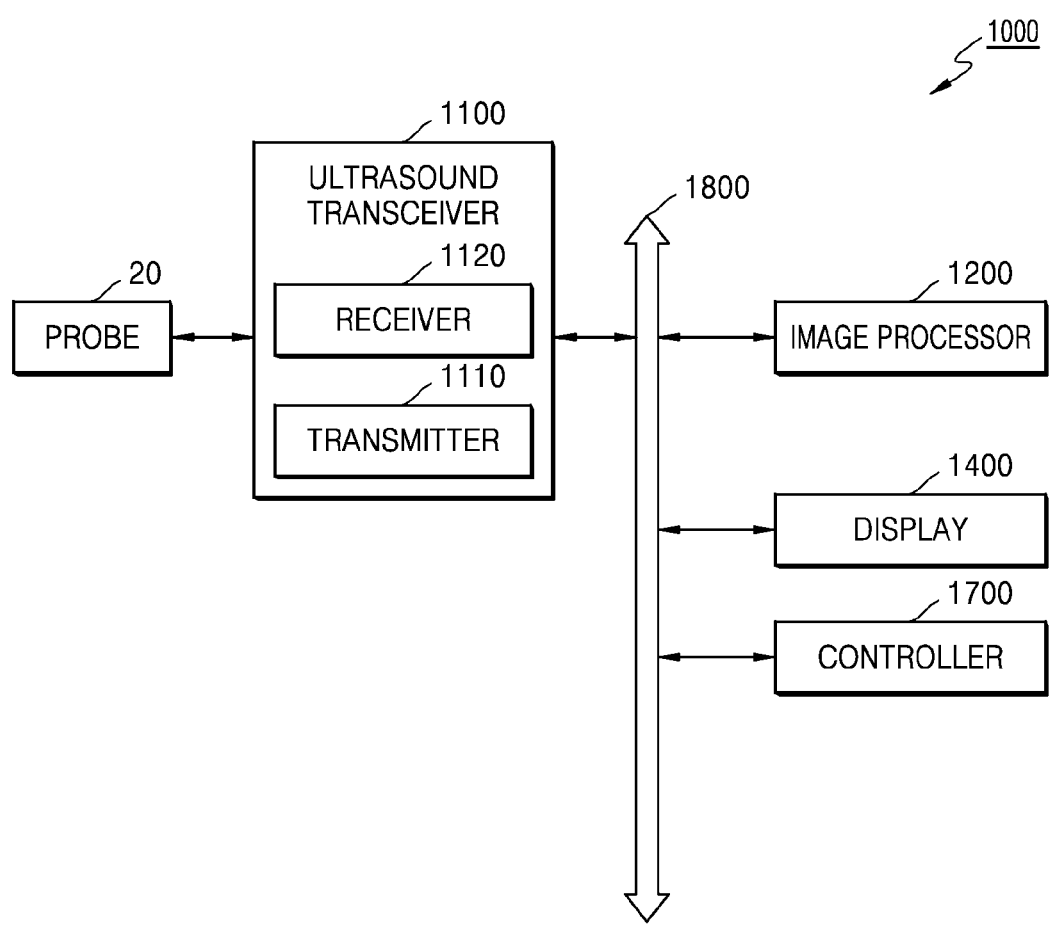
FIG. 3 is a block diagram of a structure of an ultrasound diagnosis apparatus, according to an exemplary embodiment.

FIG. 3 is a block diagram of a structure of the ultrasound diagnosis apparatus 1000, according to an exemplary embodiment.

Referring to FIG. 3, the ultrasound diagnosis apparatus 1000 includes the probe 20, the ultrasound transceiver 1100, the image processor 1200, the display 1400, and the controller 1700.

The aforementioned components will now be described in detail.

The controller 1700 controls all operations of the ultrasound diagnosis apparatus 1000.

That is, the control unit 1700 may control operations performed among the ultrasound transceiver 1100, the image processor 1200, and the display 1400 shown in FIG. 3.

All or some of the probe 20, the ultrasound transceiver 1100, the image processor 1200, the display 1400, and the controller 1700 may be operated by software modules. However, exemplary embodiments are not limited thereto, and some of the components stated above may be operate by hardware modules.

The probe 20 transmits an ultrasound signal to the object 10 based on a driving signal applied by the ultrasound transceiver 1100 and receives an echo signal reflected by the object 10.

The ultrasound transceiver 1100 transmits the ultrasound signal to the object 10 and receives a response signal to the transmitted ultrasound signal.

The transmitter 1110 of the ultrasound transceiver 1100 supplies a driving signal to the probe 20, and the receiver 1120 of the ultrasound transceiver 1100 processes the echo signal received from the probe 20 to generate ultrasound data.

For example, while a user is periodically applying a force to a diagnosis part of the object 10 by using the probe 20, the probe 20 transmits an ultrasound signal to the object 10 and receives an echo signal reflected by the object 10 that periodically repeats compression and release.

In this case, the ultrasound diagnosis apparatus 1000 processes the received echo signal to generates the ultrasound image data.

The image processor 1200 may generate an ultrasound image by scan-converting the ultrasound image data generated by the ultrasound transceiver 1100.

For example, the ultrasound image may be at least one selected from a B mode image, a Doppler image, a displacement image, and an elastography image, but exemplary embodiments are not limited thereto.

The image processor 1200 may also generate displacement image data, based on the ultrasound image data generated by the ultrasound transceiver 1100.

For example, an elasticity processor 1214 of FIG. 1 may generate displacement image data from the ultrasound image data generated by the ultrasound transceiver 1100.

In this case, the displacement image data is data related to displacement between a plurality of ultrasound image frames $F_1(i)$ (where i is a natural number $|1 \leq i \leq N$) generated based on the ultrasound data, and may be generated based on displacement between two temporally adjacent ultrasound image frames. For example, displacement between two adjacent ultrasound image frames may be calculated by using a speckle tracking method using ultrasound image data, by using a method in which RF data or demodulated voxel data uses auto-correlation and cross-correlation, or by using a sum of absolute difference (SAD).

In this case, the image generator 1220 may generate a plurality of displacement image frames $F_d(i)$ (where i is a natural number $|1 \leq i \leq N-1$), based on the displacement image data generated by the elasticity processor 1214.

The image processor 1200 may also generate elastography images, based on the displacement image frames.

For example, the elasticity processor 1214 may generate displacement data, which is data related to a displacement caused by a compression force applied to the object 10, from the ultrasound data generated by the ultrasound transceiver 1100, and perform a differentiation operation on the displacement data in a direction in which the compression force is applied to the object 10 to thereby calculate a strain of the object 10. In this case, the image generator 1220 may generate a plurality of elastography image frames $F_s(i)$ (where i is a natural number $|1 \leq i \leq N-1$) based on the strain.

Thus, the ultrasound diagnosis apparatus 1000 may generate the plurality of displacement image frames $F_d(i)$ (where i is a natural number $|1 \leq i \leq N-1$) and the plurality of elastography image frames $F_s(i)$ (where i is a natural number $|1 \leq s \leq N-1$), based on the ultrasound image frames $F_1(i)$ (where i is a natural number $|1 \leq i \leq N-1$), which are temporally consecutively acquired.

For example, the plurality of displacement image frames $F_d(i)$ (where i is a natural number $|1 \leq i \leq N-1$) may be generated based on displacement between two temporally adjacent ultrasound image frames, and the plurality of elastography image frames $F_s(i)$ (where i is a natural number $|1 \leq i \leq N-1$) may be generated by differentiating the plurality of displacement image frames $F_d(i)$ (where i is a natural number $|1 \leq i \leq N-1$) in the direction in which a force is applied.

The image processor 1200 may divide the generated plurality of elastography image frames into a plurality of sections according to a predetermined criterion. For example, the image processor 1200 may determine the plurality of elastography image frames as a plurality of frame sets according to a predetermined criterion. In this case, a plurality of elastography image frames included in one frame set may correspond to a plurality of elastography image frames included in one section. In other words, the plurality of sections according to an exemplary embodiment corresponds to the plurality of frame sets. For example, N−1 elastography image frames $F_s(i)$ (where i is a natural number $|1 \leq i \leq N-1$) may be determined as K frame sets S(i) (where i is a natural number, and $1 \leq i \leq K$) according to a predetermined criterion. In this case, a plurality of consecutive elastography image frames may be included in each frame set. For example, K frame sets may be determined, like S(1)={Fs(1), Fs(2), Fs(3), ... , and Fs(m)} and S(2)={Fs(m+1), Fs(m+2), Fs(m+3), ... }, and the concept of the K frame sets may correspond to that of the plurality of sections according to an exemplary embodiment. Accordingly, a plurality of elastography image frames included in one frame set may be a plurality of elastography image frames included in one section according to an exemplary embodiment.

For example, a plurality of elastography image frames may be divided into a plurality of sections, based on a movement of an object. This will be described in greater detail later with reference to FIGS. 7A and 7B.

The plurality of elastography image frames may be divided into the plurality of sections, based on the predetermined number of fames. This will be described in greater detail later with reference to FIG. 7C.

The image processor 1200 may generate a representative elastography image that represents each of the plurality of sections, based on at least one elastography image included in each section. In this case, the representative elastography images will be described in greater detail later with reference to FIG. 9.

A memory according to an exemplary embodiment may store an algorithm or program for processing and controlling the controller 1700, or may store data that is input to and/or output from the ultrasound diagnosis apparatus 1000. For example, the memory may store medical data related to diagnosis of an object, such as ultrasound data and an ultrasound image.

The memory according to an exemplary embodiment may store medical data related to the ultrasound image data, the displacement image data, and data related to a strain.

In this case, the data related to the strain may include quality information related to a strain of an elastography image. For example, the quality information is information about a difference between strains of the elastography image and other elastography image. The other elastography image may include at least one selected from an elastography image corresponding to a previous frame and a reference elastography image set by a user. The quality information may also include information about at least one selected from the size of a mean strain of an elastography images and a correlation coefficient of the elastography image.

The memory may include at least one type of storage medium selected from a flash memory type, a hard disk type, a multimedia card micro type, a card type memory (for example, a secure digital (SD) or extreme digital (XD) memory), a random access memory (RAM), a static random access memory (SRAM), a read-only memory (ROM), an electrically erasable programmable ROM (EEPROM), a programmable ROM (PROM), magnetic memory, a magnetic disk, and an optical disk.

The programs stored in the memory may be classified into a plurality of modules according to their functions, for example, a UI module and a touch screen module.

The UI module may provide a specialized UI, GUI, or the like that interoperates with an electronic device. Functions of the UI module would be instinctively understood by one of ordinary skill in the art in view of their names and thus detailed descriptions thereof will be omitted herein.

For example, the ultrasound diagnosis apparatus 1000 according to an exemplary embodiment may provide a UI for editing an elastography image that is to be displayed on the display 1400.

For example, a user may select, via a UI, a real time mode capable of displaying an ultrasound image on the display 1400 in real time during ultrasound photography of an object, or a review mode capable of displaying an ultrasound image stored in the memory on the display 1400 after the ultrasound photography is completed.

The display 1400 according to an exemplary embodiment may include at least one of a liquid crystal display (LCD), a thin film transistor-liquid crystal display (TFT-LCD), an organic light-emitting diode (OLED), a flexible display, and a 3D display.

When the display 1400 forms a layer structure together with a touch pad to construct a touch screen, the display 1400 may be used as an input interface as well as an output device. The touch screen may be configured to detect a touch pressure in addition to a touch input position and a touched area. The touch screen may be configured to detect a proximity touch as well as the real touch.

The display 1400 according to an exemplary embodiment may display image data that may be input to and/or output from the ultrasound diagnosis apparatus.

For example, the display 1400 according to an exemplary embodiment may display the ultrasound image generated by the image processor 1200.

For example, the ultrasound image includes at least one selected from an ultrasound B mode image, an ultrasound M mode image, an ultrasound Doppler image, an ultrasound displacement image, and an ultrasound elastography image, but exemplary embodiments are not limited thereto.

The display 1400 according to an exemplary embodiment may output the plurality of elastography image frames, which are sequentially generated.

The plurality of elastography image frames according to an exemplary embodiment may be divided into the plurality of sections, and the display 1400 according to an exemplary embodiment may output only the representative elastography image frame that represents each of the plurality of sections.

In this case, the representative elastography image that represents each section according to an exemplary embodiment may be generated based on at least one elastography image frame included in each section. For example, the representative elastography image that represents each section is generated based on a plurality of elastography image frames included in each section and quality information corresponding to the elastography image frames, and the display 1400 may provide a good-quality elastography image to a user by outputting only a representative elastography image frame corresponding to good quality information. This will be described in greater detail later with reference to FIGS. 10-13.

Operations of the ultrasound diagnosis apparatus 1000 according to an exemplary embodiment are sequentially described in detail.

FIG. 4 is a flowchart of a method of displaying a representative elastography image, according to an exemplary embodiment.

In operation 100, the ultrasound transceiver 1000 transmits an ultrasound signal to an object, and receives a response signal to the transmitted ultrasound signal to thereby acquire ultrasound image data.

In operation 110, the ultrasound diagnosis apparatus 1000 acquires displacement image data, based on the ultrasound image data acquired in operation 100.

For example, the displacement image data is data related to displacement between a plurality of ultrasound image frames $F_1(i)$ (where i is a natural number $|1 \le i \le N$) generated based on the ultrasound image data, and may be generated based on displacement between two temporally adjacent ultrasound image frames.

In operation 120, the ultrasound diagnosis apparatus 1000 generates a plurality of elastography images, based on the displacement image data acquired in operation 110.

For example, the ultrasound diagnosis apparatus 1000 may generate a plurality of displacement image frames $F_d(i)$ (where i is a natural number $|1 \le i \le N-1$), based on the displacement image data. When the displacement image data is differentiated in the direction in which compression is applied to the object, a strain of the object may be calculated. In this case, a plurality of elastography image frames $F_s(i)$ (where i is a natural number $|1 \le i \le N-1$) may be generated based on the strain.

In operation 130, the ultrasound diagnosis apparatus 1000 divides the plurality of elastography images generated in operation 120 into a plurality of sections according to a predetermined criterion.

For example, N−1 elastography image frames $F_s(i)$ (where i is a natural number $|1 \le i \le N-1$) may be determined as K frame sets S(i) (where i is a natural number, and $1 \le i \le K$) according to a predetermined criterion. In this case, a plurality of consecutive elastography image frames may be included in one frame set. For example, K frame sets may be determined, like $S(1)=\{F_s(1), F_s(2), F_s(3), \ldots, \text{and } F_s(m)\}$ and $S(2)=\{F_s(m+1), F_s(m+2), F_s(m+3), \ldots\}$, and the concept of the K frame sets may correspond to that of the plurality of sections according to an exemplary embodiment. Accordingly, a plurality of elastography image frames included in one frame set may be a plurality of elastography image frames included in one section according to an exemplary embodiment.

For example, the plurality of elastography image frames may be divided into the plurality of sections (for example, a compression section and a release section), based on a movement of the object that is estimated based on the displacement image data. The plurality of elastography image frames may be divided into the plurality of sections, based on the predetermined number of fames (e.g., 40 frames are determined for one section).

In operation 140, the ultrasound diagnosis apparatus 1000 generates a representative elastography image that represents each of the plurality of sections obtained in operation 130, based on at least one elastography image included in each of the plurality of sections and quality information of the at least one elastography image.

For example, the quality information of the elastography image is related to a strain of the elastography image, and may be information about a difference between a strain of the elastography image and a strain of an elastography image corresponding to a previous frame of the elastography image. Alternatively, the quality information of the elastography image may be information about a difference between a strain of the elastography image and a strain of a reference elastography image set by a user.

The quality information of the elastography image may include information about at least one selected from the size of a mean strain of the elastography image and a correlation coefficient of the elastography image.

For example, the representative elastography image that represents each section may be an elastography image having quality information that satisfies a predetermined condition, among a plurality of elastography image frames included in each section. The representative elastography image that represents each section may be generated by synthesizing at least one elastography image frame included in each section.

In operation 150, the ultrasound diagnosis apparatus 1000 displays, on the display 1400, the representative elastography image generated in operation 140.

For example, the display 1400 may display the representative elastography image that represents each section, in real time. The representative elastography image may be displayed together with a real-time ultrasound image.

For example, the real-time ultrasound image includes at least one selected from an ultrasound B mode image, an ultrasound M mode image, an ultrasound Doppler image, an ultrasound displacement image, and an ultrasound elastography image, but exemplary embodiments are not limited thereto.

The representative elastography image that represents each section, according to an exemplary embodiment, may be displayed together with the quality information corresponding to the plurality of elastography images included in each section.

Alternatively, the representative elastography image that represents each section, according to an exemplary embodiment, may be displayed together with displacement image data corresponding to the plurality of elastography images included in each section.

Figure 5A:
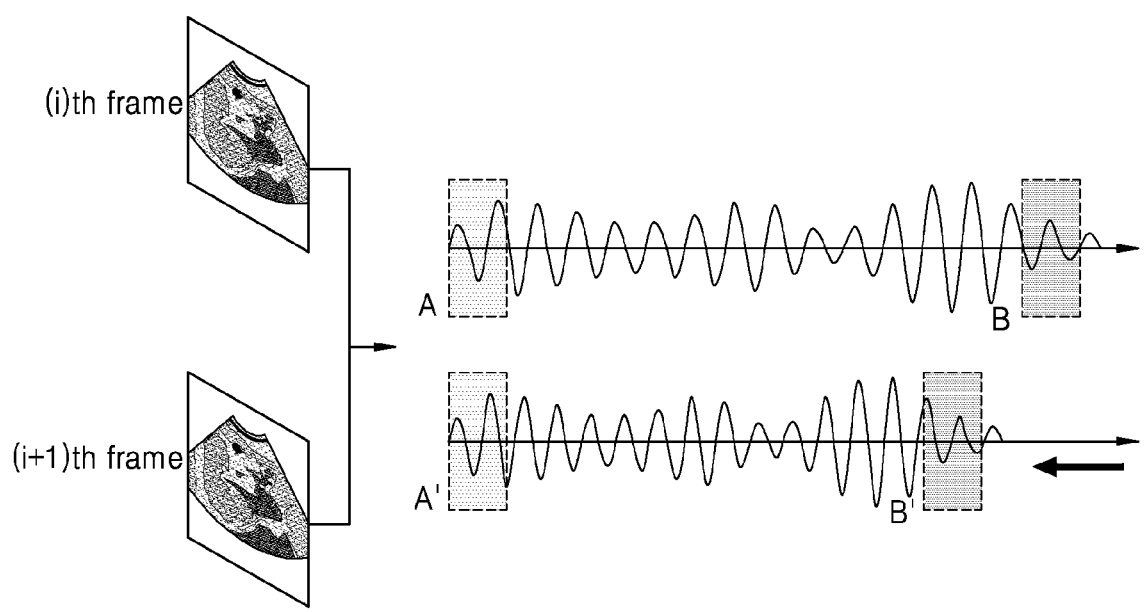
FIG. 5A is a diagram illustrating an ultrasound diagnosis apparatus comparing temporally adjacent ultrasound image frames F(i) and F(i+1) with each other and calculating a displacement caused by a tissue deformation of an object, according to an exemplary embodiment.

FIG. 5A is a diagram illustrating an ultrasound diagnosis apparatus comparing temporally adjacent ultrasound image frames F(i) and F(i+1) with each other and calculating a displacement caused by a tissue deformation of an object, according to an exemplary embodiment.

As shown in FIG. 5A, the ultrasound diagnosis apparatus according to an exemplary embodiment may calculate displacement occurring in a direction in which the object is compressed by the probe 20, from data before the object is compressed by the probe 20 and data after the object is depressed by the probe 20.

The ultrasound diagnosis apparatus according to an exemplary embodiment may calculate displacement between two temporally-adjacent ultrasound image frames by comparing ultrasound image data acquired before a user slowly compresses tissue of the object 10 by using the probe 20 as shown in FIG. 2A with ultrasound image data acquired after the user slowly compresses tissue of the object 10 with a force as shown in FIG. 2B.

For example, displacement between two adjacent ultrasound image frames may be calculated by using a speckle tracking method using ultrasound image data, by using a method in which RF data or demodulated voxel data uses auto-correlation and cross-correlation, or by using an SAD, but exemplary embodiments are not limited thereto.

For example, the precision of displacement calculation uses a resolution of no more than sub-μm, and correlation for a data window of about 0.5 to 2 mm is calculated to increase a signal-to-noise ratio (SNR). Because the value of the obtained displacement is differentiated, the displacement is sensitive to noise. Thus, when signal processing for removing noise is performed, a finally obtained strain image has a resolution of several mm.

For example, as shown in FIG. 5A, a displacement calculation model for scan line data before the compression is applied and a displacement calculation model for scan line data after the compression is applied may be obtained. As shown in FIG. 5A, compared with the data before the compression is applied (ultrasound image frame F(i)), the data after the compression is applied with a force (ultrasound image frame F(i+1)) has a shortened signal length.

For example, because a response signal starting from the surface of a transducer has displacement of zero, displacement may be calculated based on the response signal starting from the surface of a transducer. After a data window for calculating correlation is determined and displacement is calculated, displacement may be calculated again while moving the data window in a depth direction of the object. As the depth of the object increases, displacement between a signal at the ultrasound image frame F(i) and a signal at the ultrasound image frame F(i+1) increases. Thus, the displacement is previously estimated, and the data window is moved to a location capable of calculating displacement. In other words, because windows A and A' are close to each other and windows B and B' are away from each other, a data location of window B' is estimated and compared with window B.

Figure 5B:
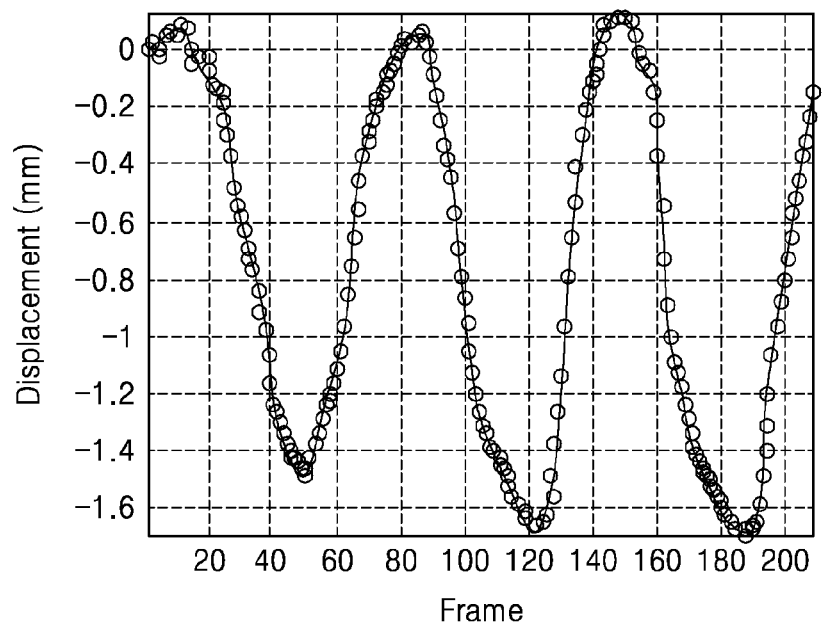
FIG. 5B is a graph illustrating displacement image data that an ultrasound diagnosis apparatus acquires for each of a plurality of temporally-consecutive frames, according to an exemplary embodiment.

FIG. 5B is a graph illustrating displacement image data that an ultrasound diagnosis apparatus acquires for each of a plurality of temporally-consecutive frames, according to an exemplary embodiment.

For example, based on displacement image data related to displacement between two adjacent ultrasound image frames among the plurality of ultrasound image frames $F_1(i)=\{i$ is a natural number $|1 \le i \le N\}$, the plurality of displacement image frames $F_d(i)=\{i$ is a natural number $|1 \le i \le N-1\}$ may be generated. In this case, the plurality of elastography image frames $F_s(i)=\{i$ is a natural number $|1 \le i \le N-1\}$ according to an exemplary embodiment may be acquired by differentiating the plurality of displacement image frames $F_d(i)=\{i$ is a natural number $|1 \le i \le N-1\}$ in the direction in which the compression has been applied to the object.

In this case, as shown in FIG. 5B, the horizontal axis represents the plurality of displacement image frames $F_d(i)=\{i$ is a natural number $|1 \le i \le N-1\}$, and the vertical axis represents displacement image data corresponding to each displacement image frame.

Alternatively, the horizontal axis of FIG. 5B may represent the plurality of elastography image frames $F_s(i)=\{i$ is a natural number $|1 \le i \le N-1\}$ obtained by performing a differentiation operation on the plurality of displacement image frames in the direction of the compression force. In this case, the plurality of elastography image frames of the horizontal axis according to an exemplary embodiment may be divided into a plurality of sections according to a predetermined criterion. This will now be described in detail with reference to FIGS. 6 and 7C.

Figure 6:
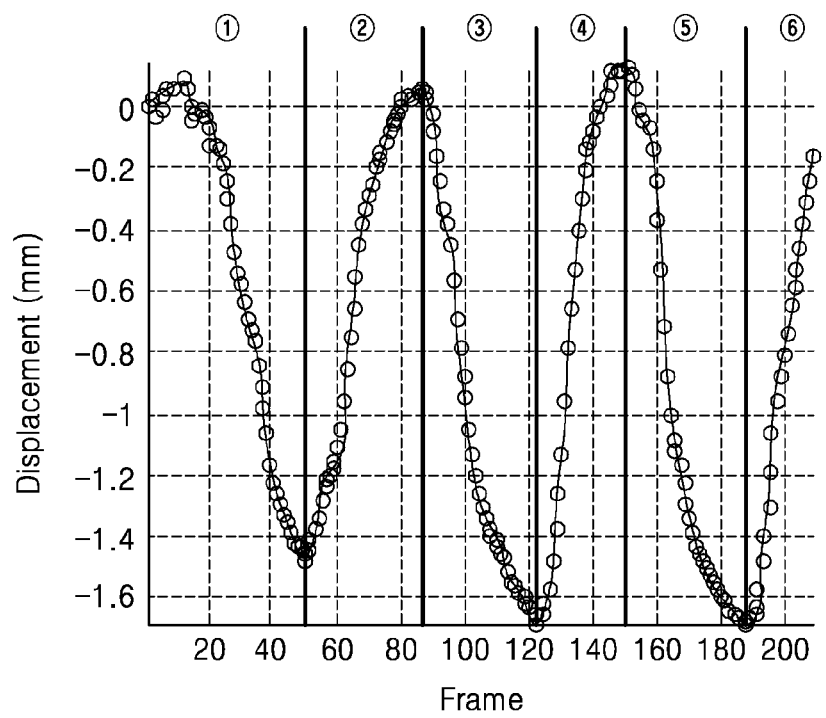
FIG. 6 is a graph illustrating an ultrasound diagnosis apparatus dividing a plurality of temporally consecutive elastography image frames into a plurality of sections according to a predetermined criterion, according to an exemplary embodiment.

FIG. 6 is a graph illustrating an ultrasound diagnosis apparatus dividing a plurality of temporally consecutive elastography image frames into a plurality of sections according to a predetermined criterion, according to an exemplary embodiment.

For example, the plurality of temporally consecutive elastography image frames according to an exemplary embodiment may be divided into first through sixth sections according to a predetermined criterion, as shown in FIG. 6.

In this case, the plurality of sections according to an exemplary embodiment corresponds to a plurality of frame sets.

For example, as shown in FIG. 6, 210 elastography image frames $F_s(i)$ (where i is a natural number $|1 \le i \le 210$) are determined as 6 frame sets S(i) (where i is a natural number, and $1 \le i \le 6$) according to a predetermined criterion. In this case, a plurality of consecutive elastography image frames may be included in one frame set.

For example, as shown in FIG. 6, 6 frame sets may be determined, e.g., S(1)={Fs(1), F$_s$(2), F$_s$(3), . . . , F$_s$(50)}, S(2)={F$_s$(51), . . . , F$_s$(92)}, S(3)={F$_s$(93), . . . , F$_s$(120)}, S(4)={F$_s$(121), . . . , F$_s$(150)}, S(5)={F$_s$(151), . . . , F$_s$(183)}, and S(6)={ F$_s$(184), . . . , F$_s$(212)}, and the concept of the 6 frame sets may correspond to that of 6 sections according to an exemplary embodiment. Accordingly, a plurality of elastography image frames included in one frame set may be a plurality of elastography image frames included in one section according to an exemplary embodiment.

In this case, the predetermined criterion may be, for example, information based on a movement of the object that is estimated based on displacement image data. Alternatively, the predetermined criterion may be the predetermined number of frames.

Figure 7A:
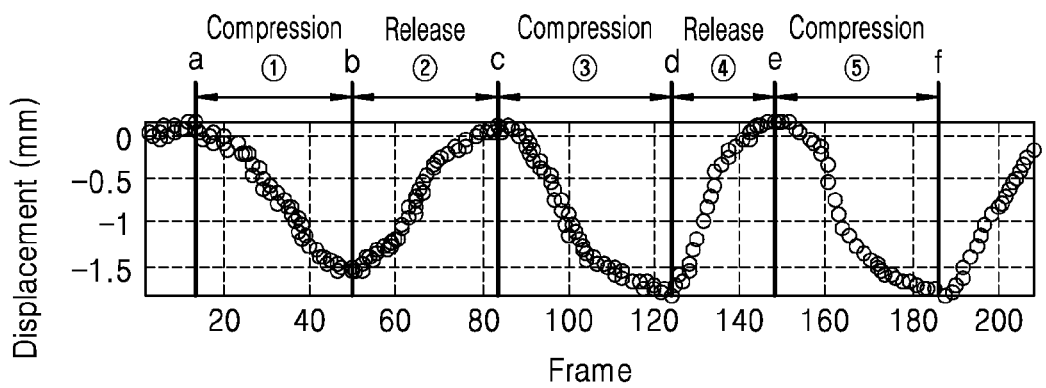
FIGS. 7A and 7B are graphs illustrating an ultrasound diagnosis apparatus dividing a plurality of elastography image frames into a plurality of sections, based on a movement of an object, according to an exemplary embodiment.
Figure 7B:
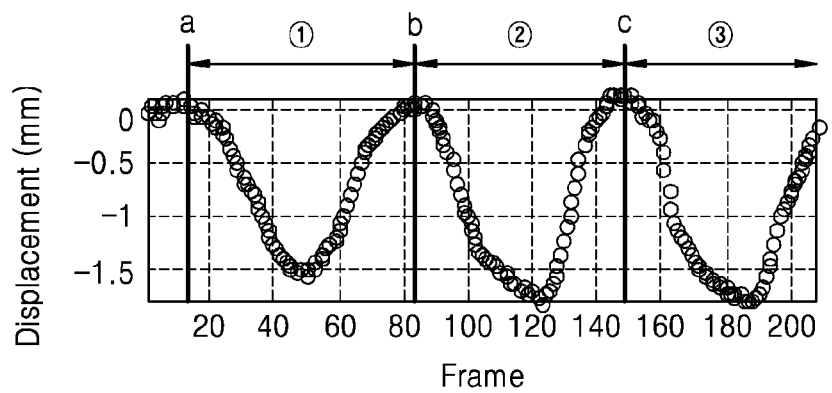

FIGS. 7A and 7B are graphs illustrating an ultrasound diagnosis apparatus dividing a plurality of elastography image frames into a plurality of sections, based on a movement of an object, according to an exemplary embodiment.

As shown in FIGS. 7A and 7B, the plurality of elastography image frames in the horizontal axis may be divided into the plurality of sections, based on displacement image data in the vertical axis.

For example, the plurality of elastography image frames of the horizontal axis may be divided into first through fifth sections as shown in FIG. 7A or first through third sections as shown in FIG. 7B, based on maximum displacements and inflection points of the displacement image data of the vertical axis.

In this case, the displacement image data may be generated based on displacement between two temporally adjacent ultrasound image frames. The ultrasound diagnosis apparatus 1000 according to an exemplary embodiment may estimate a movement of the object corresponding to deformation of tissue of the object, based on a plurality of consecutive displacement image data.

For example, when compression occurs in the object by applying a mechanical force (pressure) to tissue of the object, as shown in FIG. 5A, the data after the compression has occurred with the force (ultrasound image frame F(i+1)) has a shorter signal length than the data before the compression occurs (ultrasound image frame F(i)). Thus, displacement between two temporally adjacent ultrasound image frames has a negative value.

On the other hand, when release occurs in the compressed object by removing or weakening the mechanical force (pressure) applied to the tissue of the object, data after the release has occurred has a longer signal length than data before the release occurs. Thus, a displacement between two temporally adjacent ultrasound image frames has a positive value.

Thus, as shown in FIGS. 7A and 7B, when displacement image data when no force is applied to the object is zero, displacement when the object is compressed has a negative value. Thus, the value of the displacement image data decreases from 0 to a negative value. On the other hand, displacement when the object is released has a positive value. Thus, as shown in FIGS. 7A and 7B, the value of the displacement image data increases from a negative value to 0. In other words, the ultrasound diagnosis apparatus 1000 according to an exemplary embodiment may estimate a movement of the object, based on the displacement image data.

As shown in FIG. 7A, the plurality of elastography image frames may be divided into the first through fifth sections.

For example, the plurality of elastography image frames may be divided into sections S(1)={FS(i) |i is a natural number, a≤i≤b}, S(2)={FS(i) |i is a natural number, b+1≤i≤c}, S(3)={FS(i) |i is a natural number, c+1≤i≤d}, S(4)={FS(i) |i is a natural number, d+1≤i≤e}, and S(5)={FS (i) |i is a natural number, e+1≤i≤f}.

In this case, as shown in FIG. 7A, values of displacement image data in sections S(1), S(3), and S(5) decrease from 0 to a negative number. Thus, the sections S(1), S(3), and S(5) may be estimated as sections in which compression occurs on the object. Values of displacement image data in sections S(2) and S(4) increase from a negative number to 0. Thus, the sections S(2) and S(4) may be estimated as sections in which release occurs on the object.

As shown in FIG. 7B, the plurality of elastography image frames may be divided into first through third sections. For example, the plurality of elastography image frames may be divided into sections S(1)={FS(i) |i is a natural number, a≤i≤b}, S(2)={FS(i) |i is a natural number, b+1≤i≤c}, and S(3)={FS(i) |i is a natural number, c+1≤i≤d}.

In this case, the value of displacement image data in each of the sections S(1), S(2), and S(3) decreases from 0 to a negative number and then increases from the negative number back to 0. Thus, each of the sections S(1), S(2), and S(3) includes a cycle in which a compression force is applied to the object and then removed.

As shown in FIGS. 7A and 7B, the plurality of elastography image frames according to an exemplary embodiment may be divided into the plurality of sections, according to the movement of the object that is estimated based on the displacement image data.

Figure 7C:
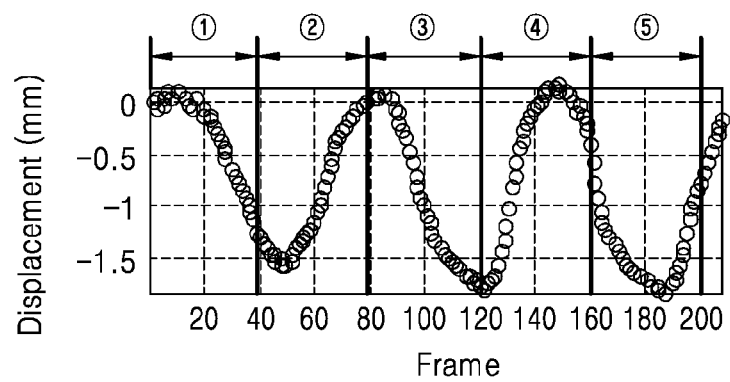
FIG. 7C is a graph illustrating an ultrasound diagnosis apparatus dividing a plurality of elastography image frames into a plurality of sections, based on the predetermined number of frames, according to an exemplary embodiment.

FIG. 7C is a graph illustrating an ultrasound diagnosis apparatus dividing a plurality of elastography image frames into a plurality of sections, based on the predetermined number of frames, according to an exemplary embodiment.

As shown in FIG. 7C, the plurality of elastography image frames may be divided into the first through fifth sections each including 40 elastography image frames.

As shown in FIG. 7C, the plurality of elastography image frames may be divided into sections S(1)={F$_s$(i) |i is a natural number, and 1≤i≤40}, S(2)={F$_s$(i) |i is a natural number, and 41≤i≤80}, S(3)={F$_s$(i) |i is a natural number, and 81≤i≤120}, S(4)={F$_s$(i) |i is a natural number, and 121≤i≤160}, and S(5)={F$_s$(i) |i is a natural number, and 161≤i≤200}.

In this case, the number of elastography image frames included in each section may be set by a user or set by default.

Figure 8:
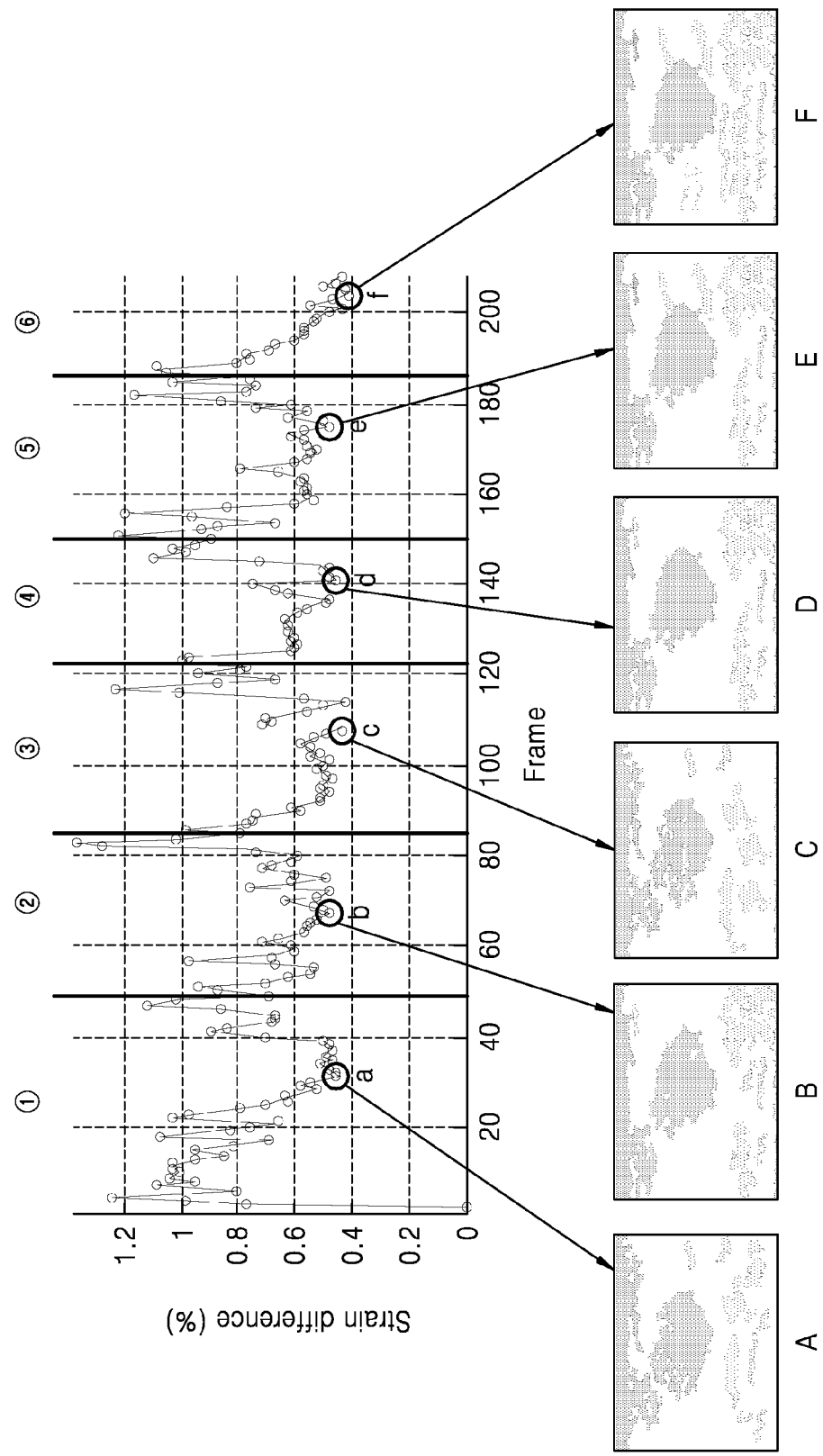
FIG. 8 is a diagram illustrating an ultrasound diagnosis apparatus selecting representative elastography images that respectively represent a plurality of sections, based on quality information corresponding to elastography images, according to an exemplary embodiment.

FIG. 8 is a diagram illustrating an ultrasound diagnosis apparatus selecting representative elastography images that respectively represent a plurality of sections, based on quality information corresponding to elastography images, according to an exemplary embodiment.

The quality information according to an exemplary embodiment includes information related to strains of the elastography images.

For example, quality information is information about a difference between strains of an elastography image and another elastography image (strain difference). The other elastography image may include at least one selected from an elastography image corresponding to a previous frame of the elastography image, and a reference elastography image set by a user.

In this case, when a strain difference between two adjacent elastography image frames is low, this means that consistency between the two adjacent elastography image frames is high, and it may be determined that quality information is high. Thus, the quality information according to an exemplary embodiment may be determined based on a strain difference, as shown in FIG. 8.

As shown in FIG. 8, a plurality of elastography image frames may be divided into first through sixth sections according to a predetermined criterion. A description of the predetermined criterion has been given above with reference to FIGS. 7A-7C, and thus will be omitted.

The ultrasound diagnosis apparatus 1000 according to an exemplary embodiment may generate a representative elastography image that represents each section, based on at least one elastography image included in each section and quality information corresponding to the at least one elastography image.

For example, the representative elastography image that represents each section may be an elastography image having quality information that satisfies a predetermined condition, among the at least one elastography image frame included in each section.

For example, the predetermined condition may be a condition of selecting, from the at least one elastography image included in each section, an elastography image frame in which a strain difference between two adjacent elastography images is minimum.

In this case, the elastography image frame in which a strain difference between two adjacent elastography images is minimum in each section may be selected as the representative elastography image that represents each section.

Alternatively, an elastography image frame in which a strain difference between the elastography image frame and a reference elastography image set by a user is minimum in each section may be selected as the representative elastography image that represents each section.

As shown in FIG. 8, an elastography image frame $F_s(a)$ having a minimum strain difference within the first section may be selected as a representative elastography image frame A, which represents the first section. Similarly, a representative elastography image frame B ($F_s(b)$) of the second section, a representative elastography image frame C ($F_s(c)$) of the third section, a representative elastography image frame D ($F_s(d)$) of the fourth section, a representative elastography image frame E ($F_s(e)$) of the fifth section, and a representative elastography image frame F ($F_s(f)$) of the sixth section may be generated.

The quality information may include information about at least one selected from the size of a mean strain of an elastography images and a correlation coefficient of the elastography image.

Figure 9:
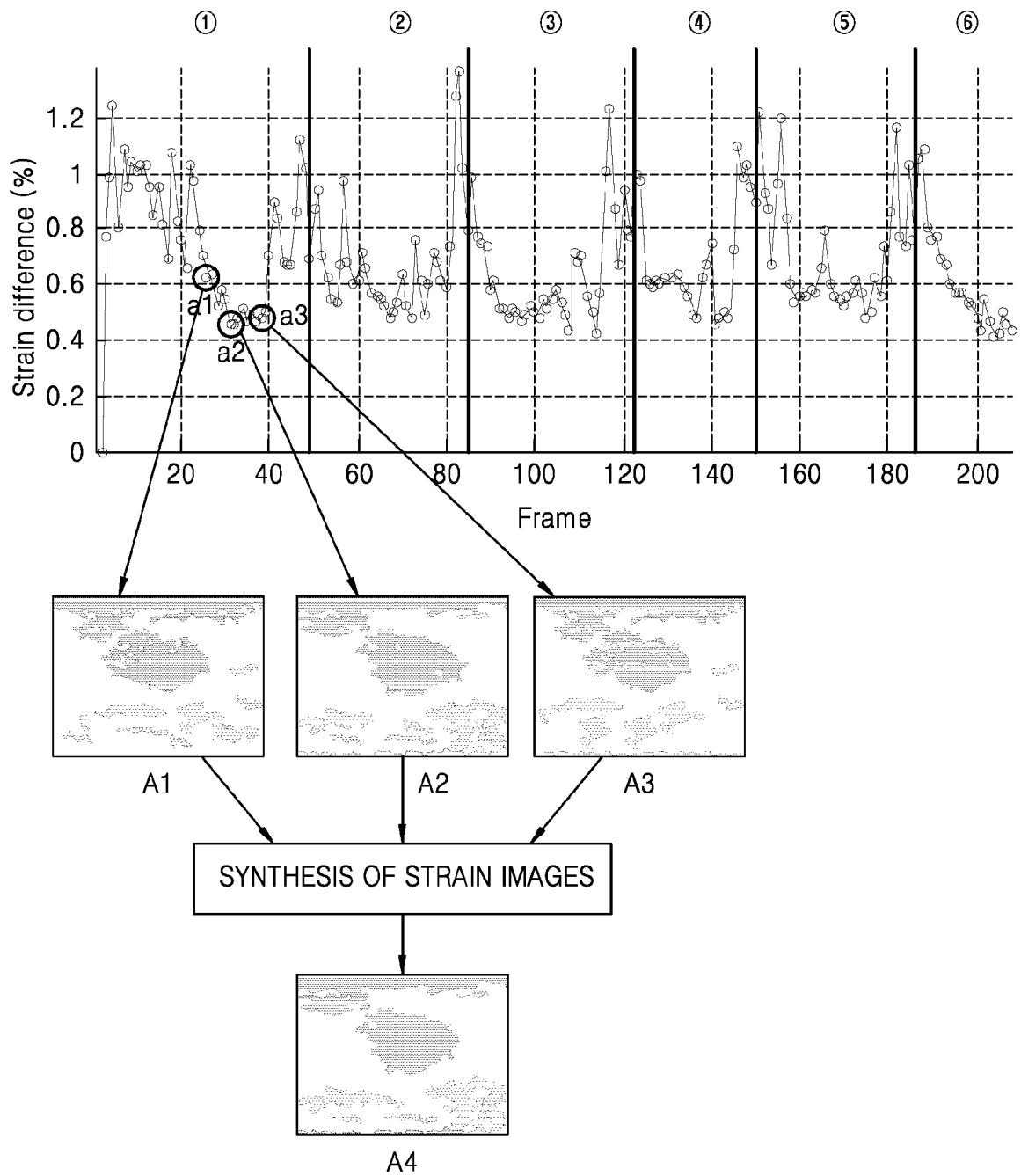
FIG. 9 is a diagram illustrating an ultrasound diagnosis apparatus generating a representative elastography image of a section by synthesizing at least one elastography image included in the section, according to an exemplary embodiment.

FIG. 9 is a diagram illustrating an ultrasound diagnosis apparatus generating a representative elastography image of a section by synthesizing at least one elastography image included in the section, according to an exemplary embodiment.

A representative elastography image that represents each section according to an exemplary embodiment may be generated based on at least one elastography image included in each section.

For example, the representative elastography image may be generated by synthesizing all of the elastography image frames included in each section. The representative elastography image may also be generated by synthesizing only elastography image frames having quality information that satisfies a predetermined condition, among a plurality of elastography image frames included in each section.

As shown in FIG. 9, a plurality of elastography image frames may be divided into first through sixth sections, and a representative elastography image frame A4 that represents the first section may be generated by synthesizing elastography image frame $F_s(a1)$, $F_s(a2)$ and $F_s(a3)$ or A1, A2, and A3 included in the first section.

A method of synthesizing a plurality of elastography image frames, according to an exemplary embodiment, may be, for example, a moving average method or a weighted average method based on quality information, but exemplary embodiments are not limited thereto.

A user may select, via a UI, a real time mode capable of displaying an ultrasound image on the display 1400 in real time during ultrasound photography of an object, or a review mode capable of displaying an ultrasound image stored in the memory on the display 1400 after the ultrasound photography is completed.

Figure 10:
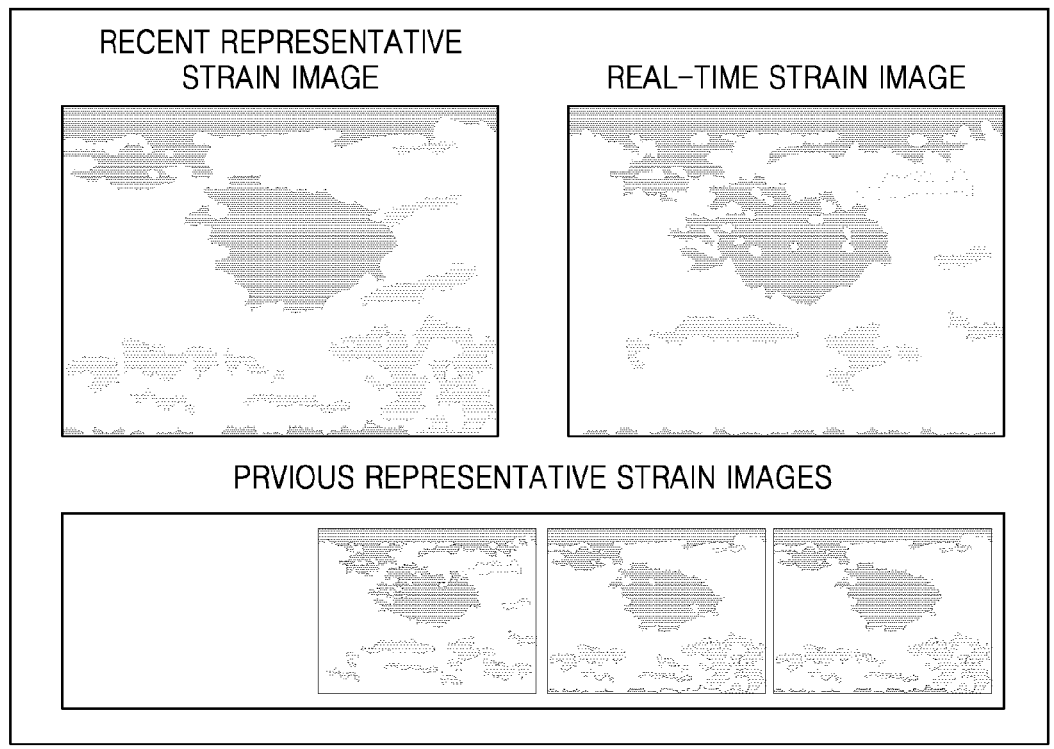
FIGS. 10 and 11 are diagrams illustrating an ultrasound diagnosis apparatus displaying representative elastography images together with a real-time ultrasound image, according to an exemplary embodiment.
Figure 11:
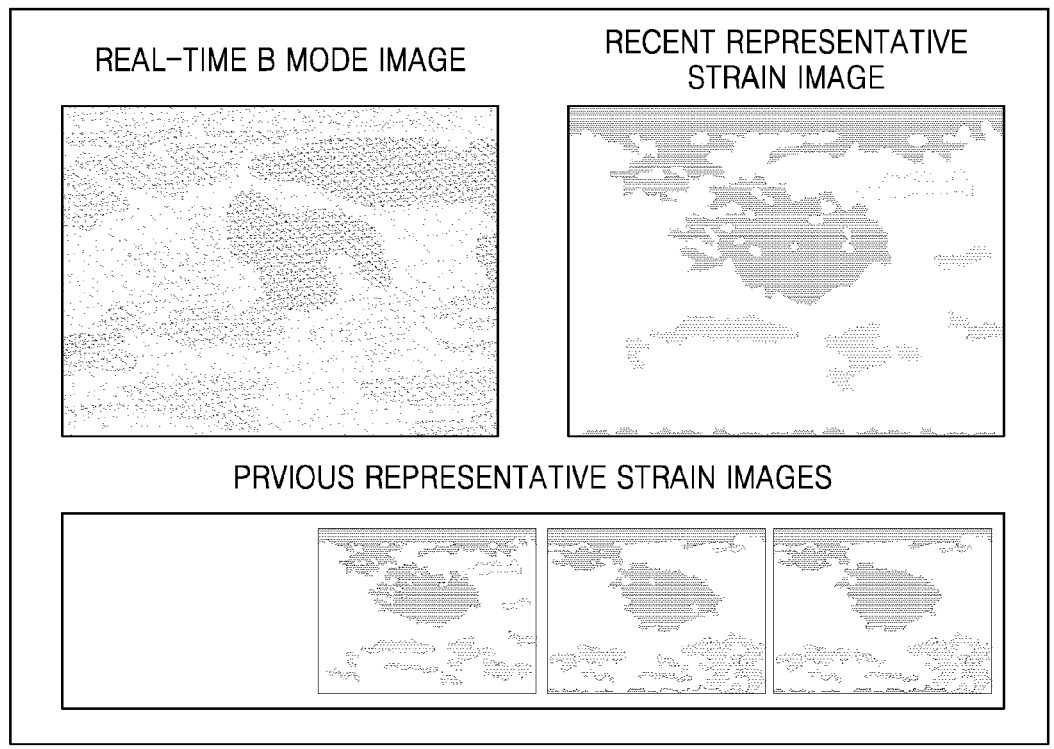

FIGS. 10 and 11 are diagrams illustrating an ultrasound diagnosis apparatus displaying representative elastography images together with a real-time ultrasound image, according to an exemplary embodiment.

The display 1400 according to an exemplary embodiment may display image data that may be input to and/or output from the ultrasound diagnosis apparatus. For example, the display 1400 according to an exemplary embodiment may display the ultrasound image generated by the image processer 1200.

For example, the ultrasound image includes at least one selected from an ultrasound B mode image, an ultrasound M mode image, an ultrasound Doppler image, an ultrasound displacement image, and an ultrasound elastography image or strain image, but exemplary embodiments are not limited thereto.

The display 1400 according to an exemplary embodiment may output a plurality of elastography image frames, which are sequentially generated. For example, the display 1400 may display a plurality of temporally consecutive elastography image frames in real time.

The plurality of elastography image frames according to an exemplary embodiment may be divided into a plurality of sections, and the display 1400 according to an exemplary embodiment may output only a representative elastography image frame that represents each of the plurality of sections. For example, the display 1400 may display the representative elastography image frame that represents each section in real time.

When each of the plurality of sections according to an exemplary embodiment ends, a currently-displayed representative elastography image according to an exemplary embodiment may be updated with a representative elastography image of a most recently concluded section. For example, when a second section ends after a first section ends, a currently-displayed representative elastography image frame of the first section may be updated with a representative elastography image frame of the second section. In this case, a plurality of representative elastography images representing a plurality of already-concluded sections may be displayed together with the updated representative elastography image in a chronological order.

The display 1400 according to an exemplary embodiment may display a real-time ultrasound image and representative elastography images together.

For example, the real-time ultrasound image may include at least one selected from a real-time elastography image as shown in FIG. 10 and a real-time B mode image as shown in FIG. 11.

Figure 12:
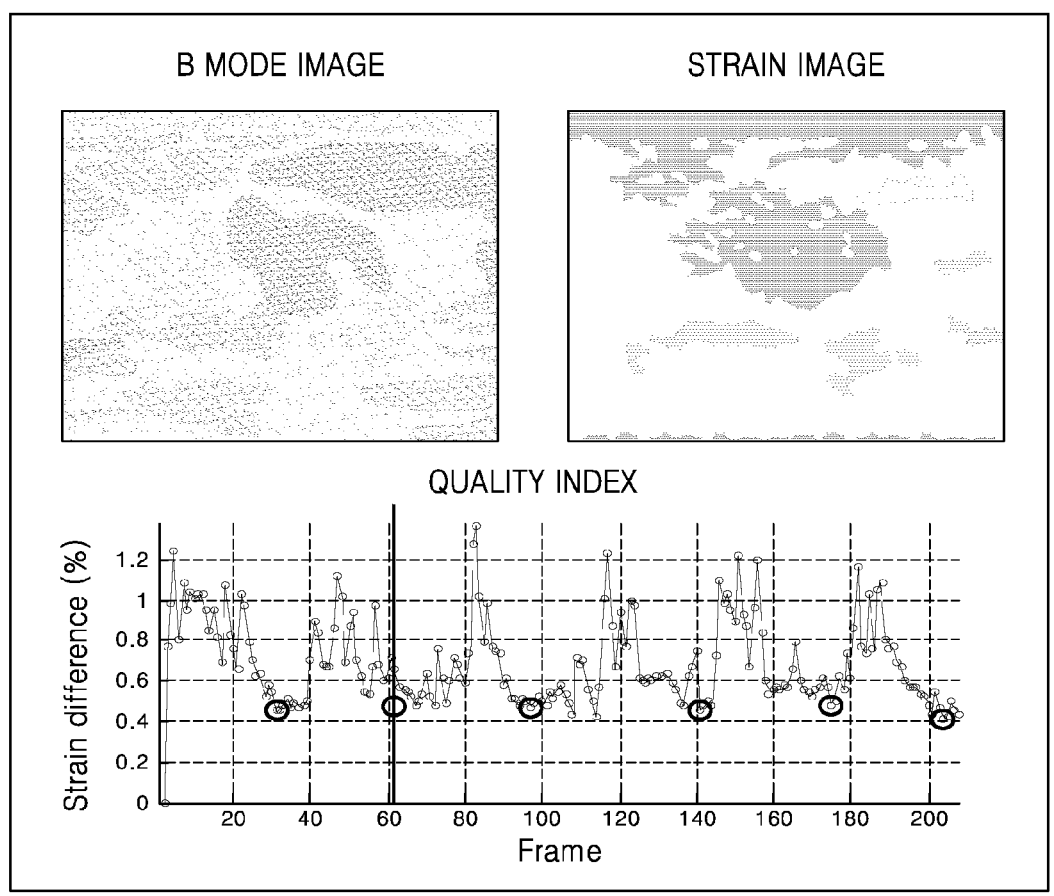
FIG. 12 is a diagram illustrating an ultrasound diagnosis apparatus displaying quality information and a representative elastography image, according to an exemplary embodiment.

FIG. 12 is a diagram illustrating an ultrasound diagnosis apparatus displaying quality information and a representative elastography image, according to an exemplary embodiment.

The display 1400 according to an exemplary embodiment may display quality information or a quality index corresponding to a plurality of elastography image frames.

For example, as shown in FIG. 12, the display 1400 may display both a representative elastography image or strain image and strain differences corresponding to the plurality of elastography image frames.

As shown in FIG. 12, while the display 1400 is outputting a representative elastography image frame, the display 1400 may also display an indicator (for example, a vertical bar) indicating that the displayed representative elastography image is an elastography image frame Fs(61) among the plurality of elastography image frames.

Figure 13:
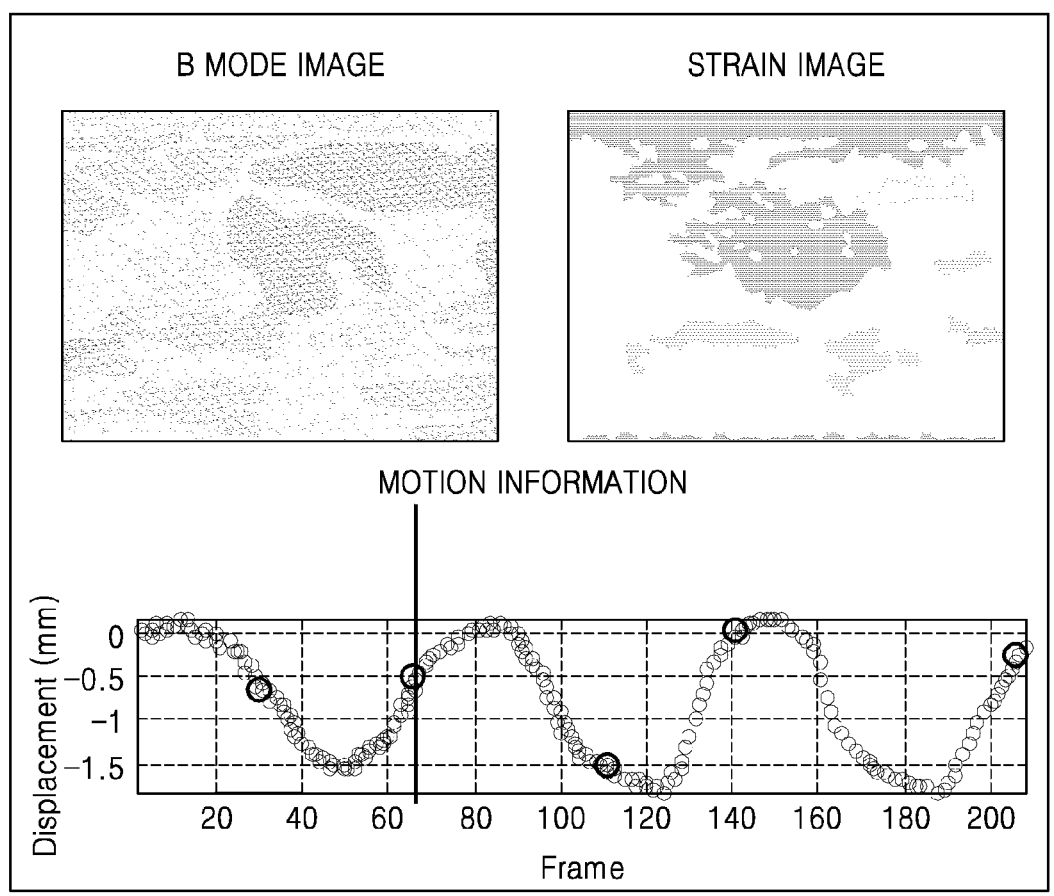
FIG. 13 is a diagram illustrating an ultrasound diagnosis apparatus displaying displacement image data and a representative elastography image together, according to an exemplary embodiment.

FIG. 13 is a diagram illustrating an ultrasound diagnosis apparatus displaying displacement image data and a representative elastography image together, according to an exemplary embodiment.

As shown in FIG. 13, the display 1400 according to an exemplary embodiment may display displacement image data or motion information corresponding to a plurality of elastography image frames For example, as shown in FIG. 13, the display 1400 may display both a representative elastography image or strain image and the displacement image data corresponding to the plurality of elastography image frames. In this case, motion information of an object (for example, compression or release) generated based on the displacement image data displayed on the display 1400 may also be displayed.

As shown in FIG. 13, while the display 1400 is outputting a representative elastography image frame, the display 1400 may also display an indicator (for example, a vertical bar) indicating that the displayed representative elastography image is an elastography image frame $F_s(63)$ among the plurality of elastography image frames.

As described above, the ultrasound diagnosis apparatus 1000 according to an exemplary embodiment may output, to the display 1400, only representative elastography images having good quality information among a plurality of elastography image frames that are acquired in real time. The ultrasound diagnosis apparatus 1000 according to an exemplary embodiment may also output at least one selected from a representative elastography image, quality information corresponding to the representative elastography image, and motion information of an object.

In addition, the exemplary embodiments may also be implemented through computer-readable code and/or instructions on a medium, e.g., a computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of displaying an elastography image, the method comprising:
   transmitting an ultrasound signal to an object;
   receiving a response signal to the transmitted ultrasound signal;
   determining ultrasound image data based on the received response signal;
   determining displacement image data based on the determined ultrasound image data;
   generating elastography images based on the determined displacement image data;
   dividing the elastography images into sections based on a criterion, wherein each of the sections corresponds to a set of frames, and the criterion used to divide the elastography images into the sections is a predetermined number of frames or information based on a movement of the object that is estimated based on displacement image data;
   determining a representative elastography image for each of the sections based on one or more elastography images in each of the sections and quality information of the one or more elastography images, the quality information being based on a strain of a first elastography image among the one or more elastography images, a size of a mean strain of the first elastography image, and a correlation coefficient of the first elastography image, wherein the quality information is high when a strain difference between two elastography images is low; and
   displaying the representative elastography image.

2. The method of claim 1, wherein the quality information comprises a difference between the strain of the first elastography image and a strain of a second elastography image different from the first elastography image, the second elastography image comprising at least one among a previous frame the first elastography image and a reference elastography image.

3. The method of claim 1, wherein the dividing comprises:
   estimating a motion of the object based on the displacement image data; and
   dividing the elastography images into the sections based on the estimated motion.

4. The method of claim 1, wherein the dividing comprises dividing the elastography images into the sections based on a number of frames in each of the sections.

5. The method of claim 1, wherein the determining the representative elastography image comprises selecting, as the representative elastography image, an elastography image having quality information satisfying a condition from the one or more elastography images in each of the sections.

6. The method of claim 1, wherein the determining the representative elastography image comprises synthesizing the one or more elastography images in each of the sections to generate the representative elastography image.

7. The method of claim 1, wherein the displaying comprises displaying the representative elastography image together with a real-time ultrasound image that is acquired based on the determined ultrasound image data.

8. The method of claim 7, wherein the real-time ultrasound image comprises at least one among a real-time elastography image and a real-time brightness mode image.

9. The method of claim 1, wherein the displaying comprises displaying a representative elastography image of a most recently concluded section among the representative elastography image of each of the sections.

10. The method of claim 1, wherein the displaying comprises displaying the representative elastography image of each of the sections in a chronological order.

11. The method of claim 1, wherein the displaying comprises displaying the representative elastography image together with quality information corresponding to each of the elastography images.

12. The method of claim 1, wherein the displaying comprises displaying the representative elastography image together with displacement image data corresponding to each of the elastography images.

13. The method of claim 1, wherein the displacement image data comprises a displacement between ultrasound image data that is determined before a tissue of the object is compressed by a probe and ultrasound image data that is determined after the tissue of the object is compressed by the probe.

14. A non-transitory computer-readable storage medium storing a program comprising instructions to cause a computer to perform the method of claim 1.

15. An ultrasound diagnosis apparatus comprising:
an ultrasound transceiver configured to:
transmit an ultrasound signal to an object;
receive a response signal to the transmitted ultrasound signal; and
determine ultrasound image data based on the received response signal;
an image processor configured to:
determine displacement image data based on the determined ultrasound image data;
generate elastography images based on the determined displacement image data;
divide the elastography images into sections based on a criterion, wherein each of the sections corresponding to a set of frames, and the criterion used to divide the elastography images into sections is a predetermined number of frames or information based on a movement of the object that is estimated based on displacement image data; and
determine a representative elastography image for each of the sections based on one or more elastography images in each of the sections and quality information of the one or more elastography images, the quality information being based on a strain of a first elastography image among the one or more elastography images, a size of a mean strain of the first elastography image, and a correlation coefficient of the first elastography image, wherein the quality information is high when a strain difference between two elastography images is low; and
a display configured to display the representative elastography image.

16. The ultrasound diagnosis apparatus of claim 15, wherein the quality information comprises a difference between the strain of the first elastography image and a strain of a second elastography image different from the first elastography image, the second elastography image comprising at least one among a previous frame of the first elastography image and a reference elastography image.

17. The ultrasound diagnosis apparatus of claim 15, wherein the image processor is further configured to:
estimate a motion of the object based on the displacement image data; and
divide the elastography images into the sections based on the estimated motion.

18. The ultrasound diagnosis apparatus of claim 15, wherein the image processor is further configured to divide the elastography images into the sections based on a number of frames in each of the sections.

19. The ultrasound diagnosis apparatus of claim 15, wherein the image processor is further configured to select, as the representative elastography image, an elastography image having quality information satisfying a condition from the one or more elastography images in each of the sections.

20. The ultrasound diagnosis apparatus of claim 15, wherein the image processor is further configured to synthesize the one or more elastography images in each of the sections to generate the representative elastography image.

21. The ultrasound diagnosis apparatus of claim 15, wherein the display is further configured to display the representative image together with a real-time ultrasound image that is acquired based on the determined ultrasound image data.

22. The ultrasound diagnosis apparatus of claim 21, wherein the real-time ultrasound image comprises at least one among a real-time elastography image and a real-time brightness mode image.

23. The ultrasound diagnosis apparatus of claim 15, wherein the display is further configured to display a representative elastography image of a most recently concluded section among the representative elastography image of each of the sections.

24. The ultrasound diagnosis apparatus of claim 15, wherein the display is further configured to display the representative elastography image of each of the sections in a chronological order.

25. The ultrasound diagnosis apparatus of claim 15, wherein the display is further configured to display the representative elastography image together with quality information corresponding to each of the elastography images.

26. The ultrasound diagnosis apparatus of claim 15, wherein the display is further configured to display the representative elastography image together with displacement image data corresponding to each of the elastography images.

27. The ultrasound diagnosis apparatus of claim 15, wherein the displacement image data comprises a displacement between ultrasound image data that is determined before a tissue of the object is compressed by a probe and ultrasound image data that is determined after the tissue of the object is compressed by the probe.

28. An ultrasound diagnosis apparatus comprising:
an image processor configured to:
generate displacement images based on displacements between ultrasound images;
generate elastography images based on differences of strains between the displacement images;
divide the elastography images into sections; and
determine a representative elastography image for each of the sections, based on one or more elastography images in each of the sections and quality information of the one or more elastography images, the quality information being based on a strain of a first elastography image among the one or more elastography images, a size of a mean strain of the first elastography image, and a correlation coefficient of the first elastography image; and a display configured to display the representative elastography image.

* * * * *